United States Patent
Ritchie et al.

(10) Patent No.: US 10,346,754 B2
(45) Date of Patent: Jul. 9, 2019

(54) METHOD AND SYSTEM FOR PSYCHOLOGICAL EVALUATION BASED ON MUSIC PREFERENCES

(71) Applicant: Sounds Like Me Limited, Geneva (CH)

(72) Inventors: David I. Ritchie, London (GB); Adrian North, Lesmurdie (AU)

(73) Assignee: Sounds Like Me Limited, Geneva (CH)

( * ) Notice: Subject to any disclaimer, the term of this patent is extended or adjusted under 35 U.S.C. 154(b) by 913 days.

(21) Appl. No.: 14/854,091

(22) Filed: Sep. 15, 2015

(65) Prior Publication Data
US 2016/0086089 A1    Mar. 24, 2016

Related U.S. Application Data

(60) Provisional application No. 62/052,217, filed on Sep. 18, 2014.

(51) Int. Cl.
| | | |
|---|---|---|
| *G06F 15/18* | (2006.01) | |
| *G06N 5/04* | (2006.01) | |
| *G06N 7/00* | (2006.01) | |
| *G16H 50/30* | (2018.01) | |
| *G06F 19/00* | (2018.01) | |
| *G06Q 30/02* | (2012.01) | |

(52) U.S. Cl.
CPC ............. *G06N 5/04* (2013.01); *G06F 19/00* (2013.01); *G06N 7/00* (2013.01); *G16H 50/30* (2018.01); *G06Q 30/02* (2013.01)

(58) Field of Classification Search
CPC .................................................... G06F 16/68
USPC ....................................................... 706/15, 45
See application file for complete search history.

(56) References Cited

U.S. PATENT DOCUMENTS

| | | | | |
|---|---|---|---|---|
| 5,930,749 | A * | 7/1999 | Maes ................ | G10L 21/0272 704/219 |
| 7,081,579 | B2 | 7/2006 | Alcalde et al. | |
| 7,982,117 | B2 | 7/2011 | Alcalde et al. | |
| 8,053,659 | B2 | 11/2011 | Alcalde et al. | |
| 8,519,249 | B2 | 8/2013 | Alcalde et al. | |
| 8,686,272 | B2 | 4/2014 | Bonet et al. | |
| 8,954,883 | B2 * | 2/2015 | Askey ................ | G06Q 30/02 715/744 |
| 2006/0212444 | A1 * | 9/2006 | Handman ......... | G06F 17/30017 |

(Continued)

OTHER PUBLICATIONS

Emery Schubert et al., "A Dynamically Minimalist Cognitive Explanation of Musical Preference: Is Familiarity Everything?" http://www.frontiersin.org/Psychology/editorialboard, Feb. 8, 2014, vol. 5, Article 38, pp. 1-8.

(Continued)

*Primary Examiner* — David R Vincent
(74) *Attorney, Agent, or Firm* — Gibb & Riley, LLC

(57) ABSTRACT

A system and method for determining users personality types, profiles, and infer the likely intent based on the users' musical taste and listening habits. The process involves identifying the listener's musical preferences and linking this to a predetermined scale within the psychological Big 5 that in turn links to a dictionary of descriptors that defines the personality type. This can be further fine tuned by knowing the persons age, gender, and many other lifestyle variables, as well as how a user may use the music.

20 Claims, 6 Drawing Sheets

(56) References Cited

U.S. PATENT DOCUMENTS

| | | | | |
|---|---|---|---|---|
| 2009/0271496 A1* | 10/2009 | Nakamura | ........ | G06F 17/30867 709/217 |
| 2013/0080371 A1* | 3/2013 | Harber | .............. | G06F 17/30752 706/50 |
| 2014/0279817 A1* | 9/2014 | Whitman | .......... | G06F 17/30035 706/52 |
| 2015/0199010 A1* | 7/2015 | Coleman | .............. | A61B 5/0006 345/156 |

OTHER PUBLICATIONS

Dr. Adrian C. North, "Wine & Song: The Effect of Background Music on the Taste of Wine", Heriot Watt University, pp. 1-7.
Amanda E. Krause et al., "Music-listening in everyday life: Devices and choice", pp. 1-28.

* cited by examiner

METHOD AND SYSTEM FOR PSYCHOLOGICAL EVALUATION BASED ON MUSIC PREFERENCES

CROSS-REFERENCE TO RELATED APPLICATIONS

This application claims priority to U.S. Provisional Application Ser. No. 62/052,217 filed Sep. 18, 2014, the complete disclosure of which is incorporated herein by reference, in its entirety.

BACKGROUND

The systems and methods disclosed herein relate generally to analyzing and using digital music compositions, and more particularly to methods and systems for determining personality characteristics based on musical likes and dislikes.

The creation of a personalization and recommendation engine starts with the recognition that music can be likened to a "Universal Language," one that need not be taught and that impacts everyone, even newborn children. There is abundant evidence that Music is so powerful that it has a fundamental physiological and psychological effect on listeners. The fact that Music impacts us in such a way means it is unsurprising that research from around the world has shown that musical taste should relate to personality types (which are themselves fundamental motivating drives).

SUMMARY

Extensive research in music psychology has been carried out on the social and applied psychology of music, in particular the relationship between pop music culture and deviant behavior in adolescence, music and consumer behavior, and the role of musical preference in everyday life.

According to a method herein, a digital database is provided. The digital database comprises digital song files. The digital song files are mathematically analyzed, using a computerized device. The mathematical analysis determines a numerical value for each of a plurality of selected quantifiable characteristics of the songs. The quantifiable characteristics comprise physical parameters based on human perception. Samples of songs selected from the database are provided to a user. The user is permitted to subjectively indicate the user's likes and dislikes for each of the samples of the songs. A music taste profile is determined for the user based on the user's likes and dislikes. The music taste profile is linked to a predetermined psychological scale based on personality theory. Personality traits are identified based on the music taste profile.

According to a computer implemented method of determining psychological evaluation based on music preferences, a digital database is provided. The digital database comprises digital song files. The digital song files are mathematically analyzed, using a computerized device. The mathematical analysis determines a numerical value for each of a plurality of selected quantifiable characteristics of the songs. The quantifiable characteristics comprise physical parameters based on human perception. Samples of two songs are selected from the database. The user is enabled to listen to both of the samples of the two songs. An indication is received of which of the samples of the two songs the user prefers. Additional samples of songs are selected, as necessary, to establish a taste vector for the user. The taste vector comprises song characteristics that the user prefers. A music taste profile is determined for the user based on the user's likes and dislikes. The music taste profile is linked to a predetermined psychological scale. Personality traits are identified based on the music taste profile.

A system herein comprises a digital database comprising digital song files, a processor operatively connected to the digital database, and a user interface operatively connected to the processor. The processor mathematically analyzes the digital song files and determines characteristic vectors for songs in the digital song files. The processor selects samples of two songs from the database and enables a user to listen to both of the samples of the two songs using the user interface. The processor receives an indication of which of the samples of the two songs the user prefers, using the user interface. The processor selects additional samples of songs, as necessary, to establish a taste vector for the user comprising song characteristics that the user prefers. The processor determines a music taste profile for the user based on the user's likes and dislikes. The processor links the music taste profile to a predetermined psychological scale. The processor identifies personality traits based on the music taste profile.

BRIEF DESCRIPTION OF THE DRAWINGS

The systems and methods herein will be better understood from the following detailed description with reference to the drawings, which are not necessarily drawn to scale and which.

DETAILED DESCRIPTION

Figure 1:
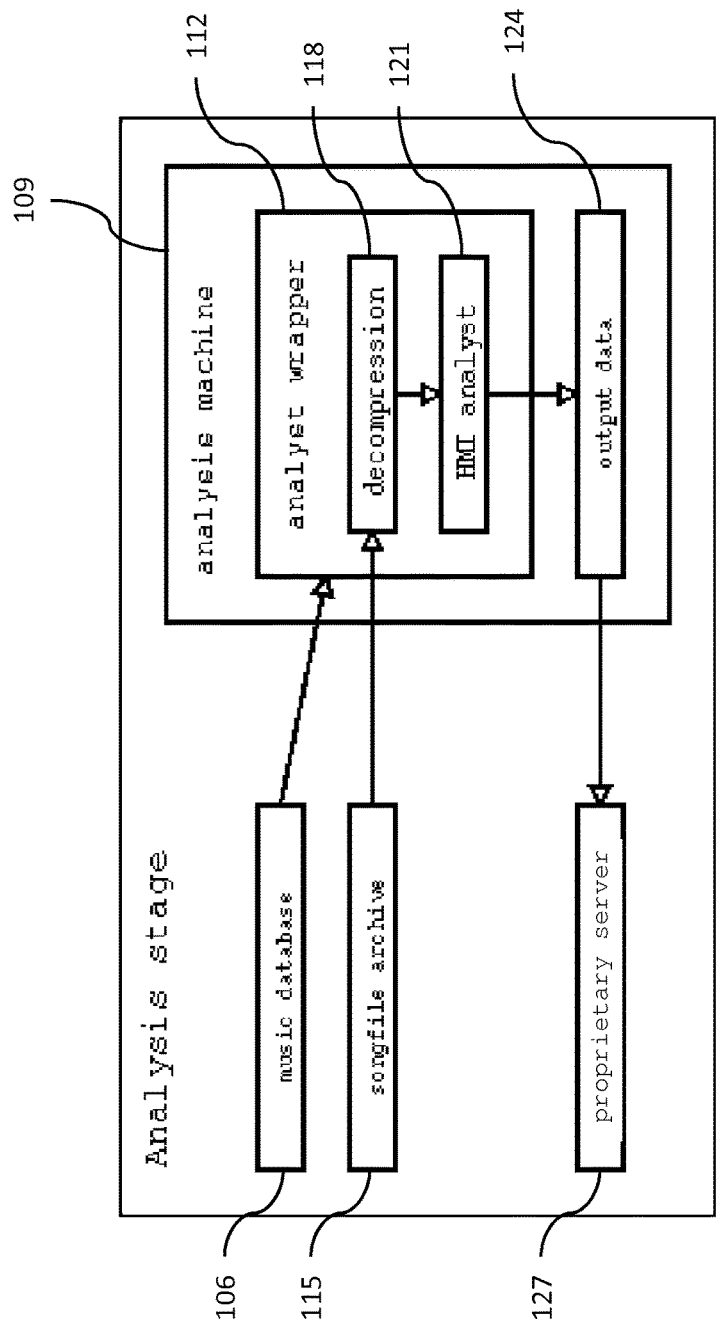
FIG. 1 is a schematic view of an exemplary system architecture according to systems and methods herein.

Systems and methods of the present disclosure employ some of the techniques for music analysis described in U.S. Pat. Nos. 7,081,579 and 8,686,272, the entire teachings of which are incorporated by reference, in their entirety.

The methods and systems described herein enable the analysis and processing of digital music files in order to establish a description of a number of characteristics of the music, create a musical characteristic profile for a user, and determine a personality profile for the user.

The raw materials for the system are music and songs. The songs may be stored in a digital file in a centralized music database or a Local Media Library. The first step performed by the system is to analyze an existing digital music file in order to create a descriptive profile for the musical characteristics of the song. The music analysis mimics human hearing and perception. In a first stage, the analysis portion reads a song file and extracts some data. This data can be represented as a series of numbers, which are the main input for future processing. Such processing depends on the final application, and can use computerized processes such as Principal Component Analysis (PCA), KNearest Neighbors (kNN), etc.

The first step performed by the system is to analyze an existing digital music file in order to create a descriptive profile for the musical characteristics of each song. Preferably, a database containing a library of digital music is provided. Such music database may be a part of the system employing the other functions described herein; it may be a remote resource that is maintained by a third party digital music company through remote, secure access; or it may comprise a personalized local media library. Access to a third party digital music library or personalized local media library may be provided, assigned, and protected under terms established by the particular third party database provider using known technology.

Whether provided as an element of the analysis and recommendation system or as a third party remote resource, the database preferably includes digital music files. The database may be modified, such as by adding additional digital music files to the database on a regular, periodic basis, such as weekly or monthly, to fit the particular business needs and objectives of the database provider. New analysis (as described herein) may also be done on a periodic basis similar to database updates, such that new music provided to the database may be included in the personality profile and recommendation functions described herein.

The processes, according to the present invention, start by analyzing a large and representative sample of music. The processes analyze more than 60 characteristics of the music, such as brightness and tempo, and measure how the characteristics change over the course of the piece of music or song in question. The selected characteristics have been identified in user testing as those producing the strongest response. Often the characteristics are perceived subconsciously by the listener, and the correct mix of parameters may be more important than any individual parameter by itself. Parameter analysis is described in U.S. Pat. No. 7,081,579 to Alcalde et al., the specification of which is included herein by reference, in its entirety.

FIG. 1 depicts a schematic view of a system architecture for enabling the transfer and processing of digital music files to an automated digital music file analysis tool in order to generate an output file that, as described in greater detail below, serves as a descriptor of the musical characteristics of the particular musical composition that was analyzed. As shown in FIG. 1, digital music files from a music database 106 may be provided to an analysis machine 109. The analysis machine 109 includes an "analyst wrapper" 112. A script for the "analyst wrapper" 112 receives digital music files from the music database 106 or a song file archive 115. The "analyst wrapper" 112 copies the particular digital music file to a location on a computer network on which the analysis system is stored, decompresses the digital music file (as shown at 118) when necessary, and passes the linear PCM file to the analysis engine 121 for processing. (In FIG. 1, the analysis engine 121 is labeled "HMI analyst"—HMI stands for Human Media Interface.) The output of such analysis engine 121 is directed to an output text file 124 that, in turn, may be used by a proprietary server 127 to conduct the utilities described below.

During the initial analysis performed by the system, all songs that are to be analyzed are processed in the same way. The particular list of songs to be processed may vary depending upon the application. For instance, for a particular user, only their own music catalogue may be analyzed. The purpose of the initial analysis performed by the system is to analyze a variety of physical parameters of the music stored in the target digital music database 106. Such physical parameters describe quantifiable characteristics of music that may be mathematically modeled to create a descriptive, electronic "footprint" for each song. Moreover, the analyzed parameters are based on human perception, and the system is referred to as a Human Media Interface (HMI) system. The characteristics have been identified to be the ones that produced the strongest reaction in testers. Often the listener detects the characteristics unconsciously. In general, the mix of parameters is more important than any individual parameter. To implement the methods described herein, the system particularly analyzes one or more of the following characteristics for each musical composition: brightness, bandwidth, volume, tempo, rhythm, low frequency, noise, octave, and how these characteristics change over the course of each piece of music or song, as well as length of the audio data. Not all of the characteristics necessarily provide distinctions in the music. Combinations of some or all of these characteristics may be employed without departing from the spirit and scope of the instant invention.

The starting point of the systems and methods described herein is the ability to extract quantitative information from a song stored in digital format. The different types of mathematical procedures used to extract song descriptor are described in detail in U.S. Pat. No. 7,081,579. The input for analysis is a list of songs with their respective descriptors (set of real numbers that could define different type of signal analysis, for example, the mean frequency, the level of noise, the mean power, tempo, rhythm, beat, etc.). A unique identifier is assigned to each song, which is used to retrieve metadata from the database, such as artist name, song title, 30-second clip, etc.

Figure 2:
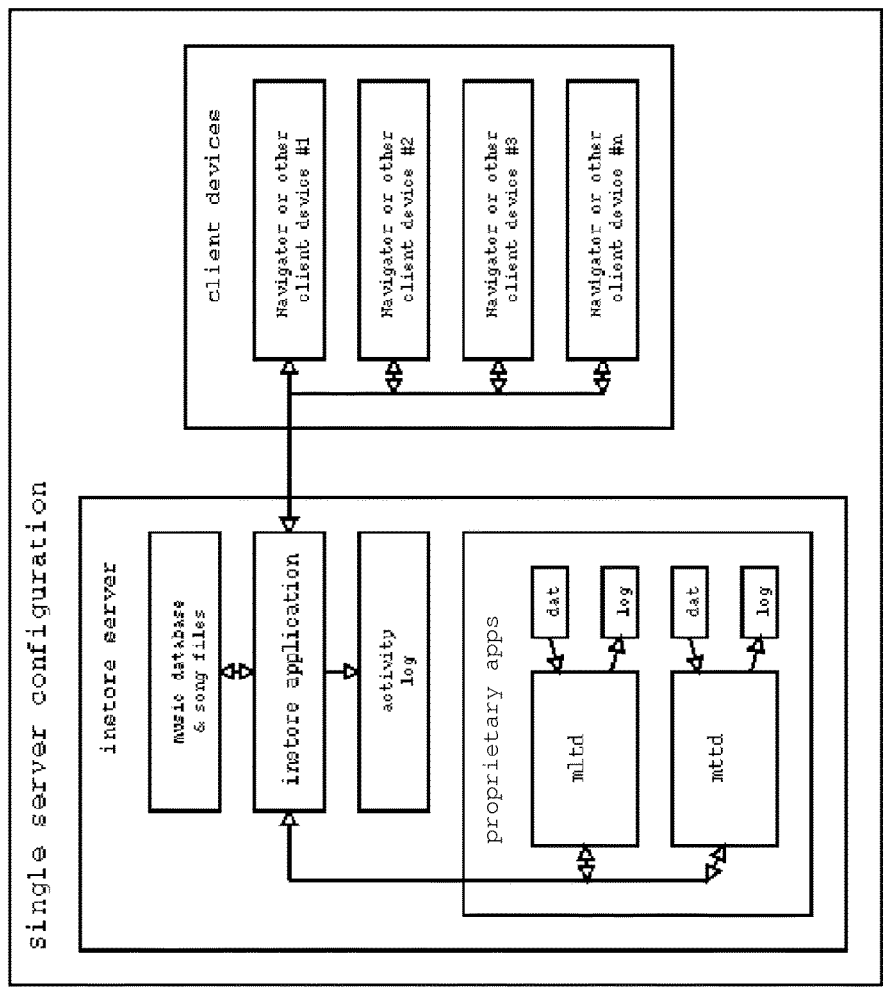
FIG. 2 is an exemplary single server configuration according to systems and methods herein.
Figure 3:
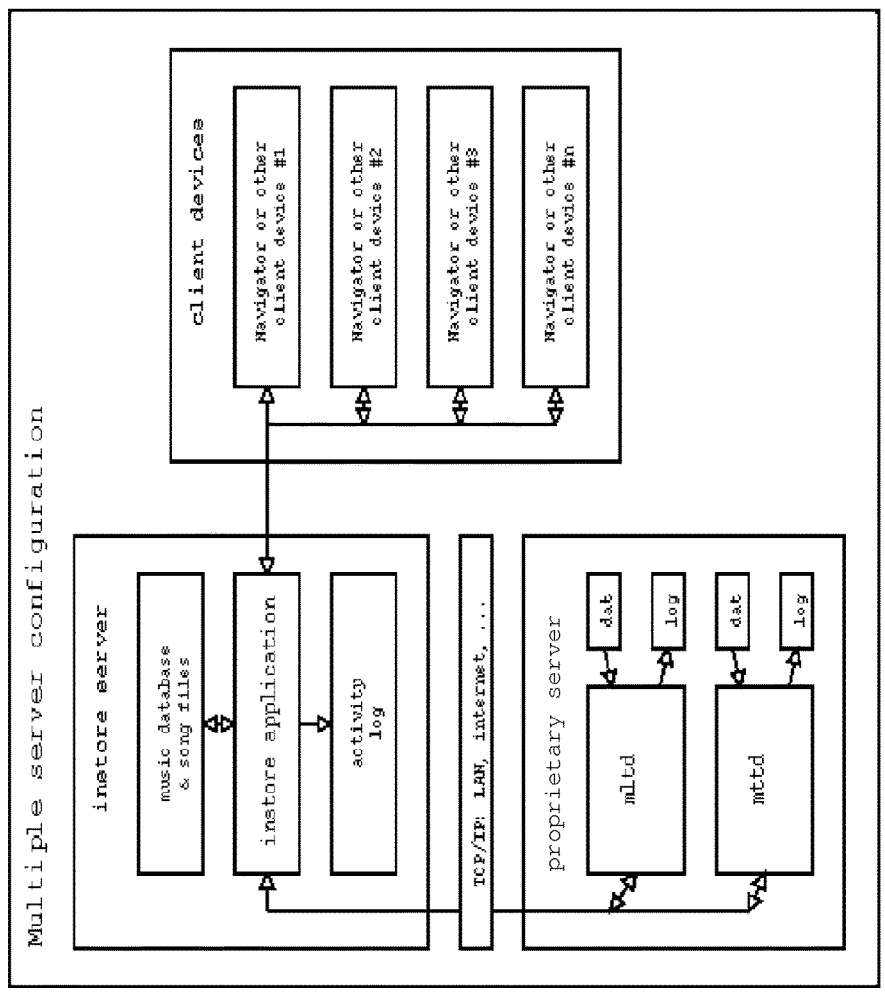
FIG. 3 is an exemplary multiple server configuration according to systems and methods herein.

The output from the analysis process for the complete song may be stored in a plain text format, tab-delimited. The next step following analysis and profiling of the library of songs is to provide a recommendation engine to enable the system to recommend songs to particular users based upon the musical characteristics of the songs as depicted by their song vectors. A song vector is a list of numerical values for each of a plurality of selected quantifiable characteristics for each digital song file. The quantifiable characteristics are physical parameters based on human perception. It should be noted that such recommendation functionality may be provided as an "in store" application running on the same server as the analysis component; on a server at the same location as the database of song parameter vectors, as illustrated in FIG. 2; on a remote server in communication with an application server at a retail location across a TCP/IP connection, as illustrated in FIG. 3; on a hand-held device, as an application; or the like. In each instance, the recommendation engine loads the parameter vector file, and is configured to particularly deal with the text format of the parameter vector file. The text data of the parameter vector file may be loaded during the recommendation engine startup by specifying so on the command line, or a command may be sent after startup to locate and load the data.

Irrespective of the locality of the software, the music recommendation functions are preferably executed as a series of requests and responses handled by a daemon (or service) on a server. The daemon listens for requests to its network address on a specific port, and communicates with client devices using its own protocol, which is a protocol designed to satisfy the functionality given by the system over any TCP/IP network, and is used to send and receive a variety of requests, including, but not exclusive to, "Music Taste Test Request" (MTT) and "More Like This Song" (MLT), as described in greater detail below.

Following analysis of the sonic parameters, software modules according to a preferred embodiment of the present invention learn a user's musical preferences. The system recognizes which parameter(s) provide distinguishing characteristics and uses the user input to select another two choices in order to capture the taste of the user regarding all of the variable parameters.

After the system has learned a user's musical preferences, it can connect the user with music selections based on his or her likes and dislikes. Further, according to devices and methods herein, the user's musical preferences may be used to establish a personality profile for the user.

The learning process of the MTT function seeks to achieve the highest possible confidence level for all parameters, in essence achieving a high confidence level for the user's preferences. In other words, the system seeks to reach a high confidence level for each user and develops a precise taste profile for each user (based on the parameters analyzed). In reality, however, this process can continue endlessly, as the MTT function seeks to shorten preferred ranges and modify preferred values. For commercial applications, it is necessary to set a limit on the MTT process. This limit can be set either by setting a limited number of sound clip comparisons, target confidence level, or both. This is a matter of simple programming on the front-end application on the customer's side.

A user's profile may be stored in the system while the user is still connected to the system. When the session is terminated, the user profile may be eliminated. However, this profile can also be saved within the system or external database and accessed at a later date, depending upon the specific retail customer and implementation environment. Thus, a user can go back, continue the MTT process, and obtain refined recommendations. This functionality may be achieved using an appropriate identification technology, such as loyalty cards or cookies. In addition, the system disclosed herein can monitor and store all user activity in a database such that identification may also be achieved via user accounts.

Once the MTT function has been completed, the user's particular musical tastes are established in the user's personal 'taste' vector. The system may use the 'taste' vector to determine and display a list of songs that matches the user's determined musical taste. Alternately, the list of matching songs or music may be displayed to the user at his or her request before completion of the analysis, in which case the recommendations will simply reflect the MTT function's current confidence level. To generate the list of matching songs, the MTT function searches the music database in order to find songs that most closely match that user's 'taste' profile. Closeness of a song to the 'taste' vector is determined by the arithmetical distance between the respective scores of the taste profile and candidate songs or music for each of the characteristics analyzed by the system.

The "More Like This" (MLT) function is implemented through a pattern-recognizing artificial intelligence system using an MLT daemon (labeled 'mltd' in FIGS. 2 and 3). The MLT function allows a user to receive music recommendations by selecting a song and requesting songs that are sonically similar to that song based on mathematical analysis of the songs. That is, the similarity is based on the Euclidean distance between characteristic vectors for the songs. Within the implementation environment, the user needs to enter the name of a song into the device or simply click on a "More Like This" button to receive recommendations.

When the MLT function is operable, the system performs real-time MLT recommendations by looking for song files that have the most similar analysis data to the parent song. The MLT lookup process consists of searching for similar songs by checking the relative distances between all parameters for each song. It is the difference between parameters that determine if the songs are similar or not for the user. Therefore, given a list of songs, each song can have a "More Like This" link to similar music.

Personal preferences can be determined by the methods for capturing personal preferences and music tastes of listeners or users as described in U.S. Pat. No. 7,081,579. A dimensional graphical projection of a three-dimensional array or galaxy of songs may be used for optimizing viewing of the corpus or universe of songs in order to facilitate the capturing of user tastes. Discovery and delivery of recommendations is described in U.S. Pat. Nos. 7,982,117; 8,053,659; and 8,519,249, the disclosures of which are incorporated herein by reference.

Cultural preferences and/or social preferences can be extracted from network information as contextual enriching information from the vector space of the song universe into the similarity measure.

Figure 4:
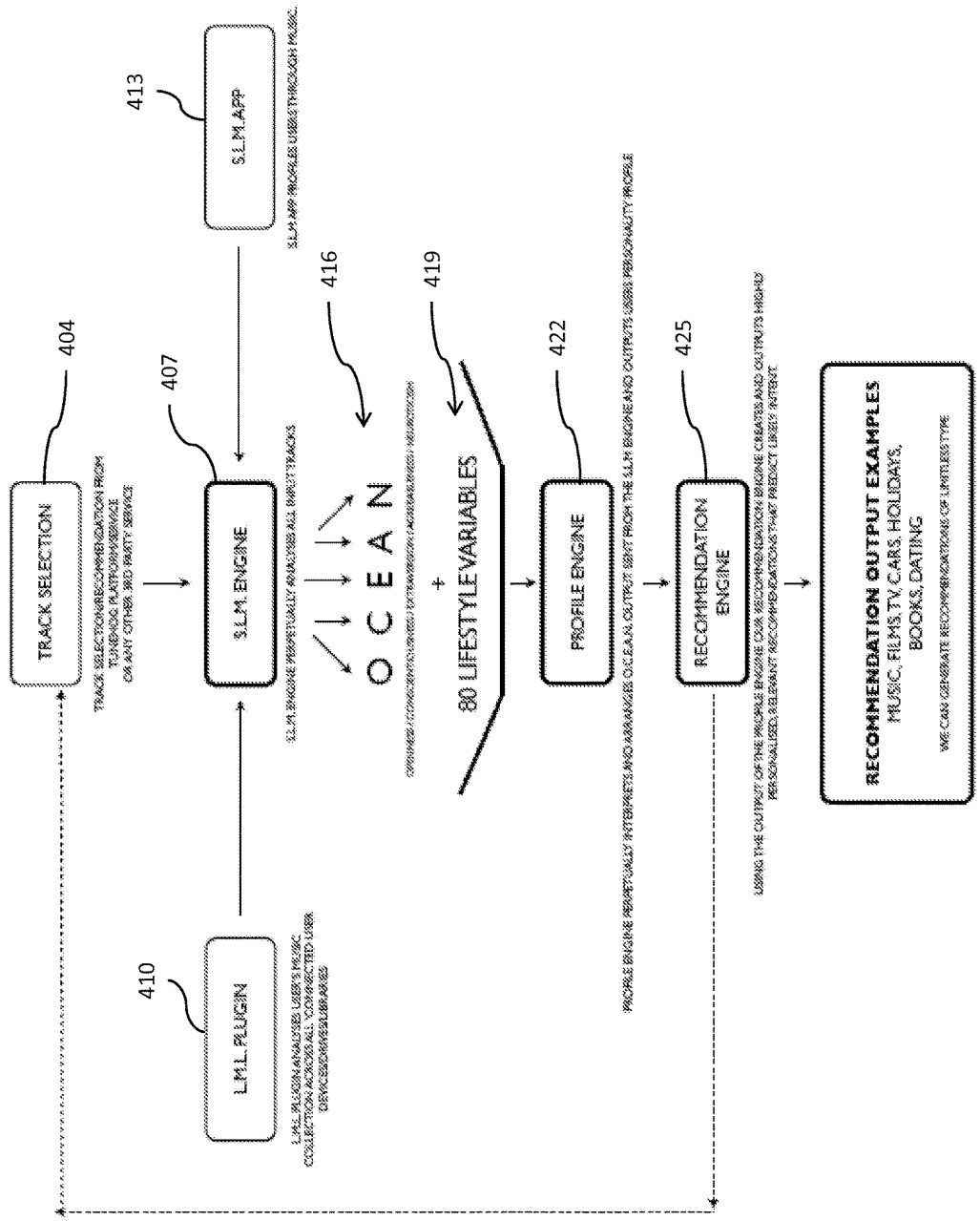
FIG. 4 illustrates a process for psychometric evaluation according to systems methods herein.

Referring to FIG. 4, musical recommendation and/or track selection 404 may be determined as described above. Inputs to the SLM (Sounds Like Me) Engine 407 may be taken from a Sonic Engine providing track selection 404, a LML (Local Media Library) plugin 410, or a SLM app 413. The LML plugin 410 may be a web-based application that reads a device's storage, hard drive, external storage device, or the like, and obtains the user's media history. The LML plugin 410 analyses a user's music collection across all connected devices and/or libraries. The LML plugin 410 also allows the methods described herein to work offline. The SLM app 413 may be a web-based application that pushes pairs of music tracks to the user and asks that they choose a preference, as described above. The SLM app 413 may also be implemented as a mobile application for handheld devices, smartphones, tablets, etc. The SLM app 413 may be used together with a number of additional profilers to show how a user uses music (i.e., a fast track way of determining their tastes and habits).

The SLM Engine 407 analyzes the input tracks according to psychometric analysis using the psychological "Big 5". In psychology, the Big 5 personality traits are five broad domains or dimensions of personality that are used to describe human personality. The theory based on the Big Five factors is called the five-factor model (FFM). The five factors are openness, conscientiousness, extraversion, agreeableness, and neuroticism—OCEAN 416. Other acronyms commonly used to refer to the five traits collectively include OCEAN, NEOAC, or CANOE. Beneath each global factor, a cluster of correlated and more specific primary factors are found; for example, extraversion includes such related qualities as gregariousness, assertiveness, excitement seeking, warmth, activity, and positive emotions.

The Big 5 model is able to account for different traits in personality without overlap between these traits. Empirical research has shown that the Big 5 personality traits show consistency in interviews, self-descriptions, and observations. Moreover, this five-factor structure seems to be found across a wide range of participants of different ages and of different cultures.

A summary of the factors of the Big 5 and their constituent traits, such that they form the acronym OCEAN:

Openness to experience: (inventive/curious vs. consistent/cautious). Appreciation for art, emotion, adventure, unusual ideas, curiosity, and variety of experience. Openness reflects the degree of intellectual curiosity, creativity, and a preference for novelty and variety a person has. It is also described as the extent to which a person is imaginative or independent, and depicts a personal preference for a variety of activities over a strict routine. Some disagreement remains about how to interpret the openness factor, which is sometimes called "intellect" rather than openness to experience.

Conscientiousness: (efficient/organized vs. easy-going/careless). A tendency to be organized and dependable, show self-discipline, be hardworking, act dutifully, aim for achievement, and prefer planned rather than spontaneous behavior.

Extraversion: (outgoing/energetic vs. solitary/reserved and introverted). Energy, positive emotions, urgency, assertiveness, sociability and the tendency to seek stimulation in the company of others, and talkativeness.

Agreeableness: (friendly/compassionate vs. analytical/detached). A tendency to be compassionate, gentle, and cooperative rather than suspicious and antagonistic towards others. It is also a measure of one's trusting and helpful nature, and whether a person is generally well tempered or not.

Neuroticism: (sensitive/nervous vs. secure/confident). The tendency to experience unpleasant emotions easily, such as anger, anxiety, depression, and vulnerability. Neuroticism also refers to the degree of emotional stability and impulse control and is sometimes referred to by its low pole, "emotional stability" or "at ease".

The five factors, OCEAN 416 analyses may be combined with several lifestyle variables 419 to provide input to a profile engine 422. The Profile Engine 422 interprets and arranges the output of the OCEAN 416 analyses that come from the SLM Engine 407. The Profile Engine 422 outputs a personality profile associated with the user based on music likes and dislikes. Methods herein have identified and linked those tracks/styles to triggers within each of the BIG 5 dimensions—OCEAN (Openness, Conscientious, Extrovert, Agreeableness, and Neuroticism).

In general, liking for a range of musical styles correlates with different big five dimensions, including but not limited to the following:

Liking for Blues is positively related to scores for self-esteem, creativity, outgoing, and at ease.

Liking for Jazz is positively related to scores for self-esteem, creativity, outgoing, and at ease.

Liking for Classical music is positively related to scores for self-esteem, creativity, introvert, and at ease.

Liking for Rap is positively related to scores for high self-esteem and outgoing.

Liking for Opera is positively related to scores for self-esteem, creativity, and gentle.

Liking for Country and Western is positively related to scores for hardworking and outgoing.

Liking for Reggae is positively related to scores for self-esteem, creativity, outgoing, gentle, and at ease, and negatively related to scores for hardworking.

Liking for Dance music is positively related to scores for creativity and outgoing, and negatively related to scores for gentle.

Liking for Indie music is positively related to scores for creativity, and negatively related to scores for self-esteem, hard working, and gentle.

Liking for Bollywood is positively related to scores for creativity and outgoing.

Liking for Rock/Heavy Metal is positively related to scores for creativity, gentle, and at ease, and negatively related to scores for self-esteem, hard-working, and outgoing.

Liking for Chart Pop is positively related to scores for self-esteem, hardworking, outgoing, and gentle, and negatively related to scores for creativity and at ease.

Liking for Soul is positively related to scores for self-esteem, creativity, outgoing, gentle, and at ease.

The Recommendation Engine 425 uses the outputs from the Profile Engine 422 and creates highly personalized, relevant recommendations that predict likely intent. Such recommendations may be based on preferences and personality. Recommendations may be related to music, films, television, books, and partners; specific instances of content for these media (such as specific television shows); other lifestyle choices, such as leisure interests (e.g., interest in various leisure time activities, such as gardening; preferences for different classes of commercial products and brands; or optimal methods of advertising and otherwise advocating to users these various media contents, leisure interests, and commercial products.

The Recommendation Engine 425 provides the ability to determine a person's personality types, profiles, and likely intent based on their musical taste and listening habits. As described herein, the process involves identifying the listener's musical preferences and linking this to a predetermined profile defined in terms of the Big 5 that in turn links to a dictionary of descriptors that defines the personality type. This can be further fine tuned by knowing the person's age i.e. younger vs. older and sex and the goal of their music usage.

The breadth and depth of the process dramatically increases the chances of accurately matching someone's music tastes and listening habits, and therefore applying the profile engine 422 in order to determine their personality type and intent and, in turn, make more accurate recommendations not limited to just music.

According to systems and methods herein, an analysis engine takes those trigger outputs and then collates them in order to produce a profile based on the determined personality type. From this we can make recommendations and infer the likely intent of that type and map it back into the engine, correcting and improving in real time.

Openness

One study looking at how personality traits affect music-induced emotion found that of all the traits, openness to experience was the best predictor of higher emotionally intense reactions to sad and slow music. The most common feelings described from sad music were nostalgia, peacefulness, and wonder, and openness to experience correlated positively with all these feelings. Sad music has also been theorized to allow for greater experience of aesthetic experiences and beauty. Furthermore, open individuals show a preference for diverse musical styles, but do not necessarily prefer popular forms of contemporary music, indicating that there are limits to this openness. However, this is only true up to a certain point, as another study looked at music's ability to produce "chills" in the listeners. Although this study found that openness was the best predictor of genre preference, there is no way to use openness to experience to predict who gets chills from music. Instead, the only measure for that was frequency of listening to music and the self-rated value of the importance of music in one's life.

Conscientiousness

Conscientiousness is negatively correlated with liking for intense and rebellious music, such as rock and heavy metal music. While previous studies have found a relationship between conscientiousness and emotional regulation, these results do not necessarily apply cross culturally.

Extraversion

Extraversion is another good predictor of music genre preference and music use. Extroverts appear to prefer happy, upbeat and conventional music, as well as energetic and rhythmic music, such as rap, hip-hop, soul, electronic, and dance music. Additionally, extraverts tend to listen to music more and have background music present in their lives more often. One study compared introverts and extroverts to see who would be more easily distracted by background music with and without lyrics. It was assumed that since extroverts listen to background music more they would be able to ignore it better when they so wished, but that was not supported by findings. No matter how much music people listen to, they are still equally affected and distracted by music with lyrics. Extroverts also prefer cheerful music with fast tempos, many melodic themes, and vocals. They are more likely than others to listen to music in the background while doing other activities, such as running, being with friends, or studying. This group also tends to use music to counter the monotony of everyday tasks, such as ironing. In one study, researchers found that extroverts preferred rock, pop, and rap because these genres facilitated dance and movement.

Agreeableness

Agreeable individuals preferred upbeat and conventional music. Additionally, listeners with high agreeableness displayed an intense emotional response to music that they had never before listened to. Agreeableness is also a good predictor of the emotional intensity experienced from all types of music, both positive and negative. Those scoring high in agreeableness tend to have more intense emotional reactions to all types of music.

Neuroticism

The more neurotic a person is, the less they like intense and rebellious music (such as rock and heavy metal), but prefer upbeat and conventional music, like country, sound tracks, and pop music. Additionally, neuroticism is positively correlated with emotional use of music. Those who scored high in neuroticism were more likely to report use of music for emotional regulation and experience higher intensity of emotional affect, especially negative emotion.

Additional Factors

Other situations have been shown to influence an individual's preferences for certain types of music. Participants in a study from 1996 provided information about what music they would prefer to listen to in given situations, and indicated that the situation greatly determined their musical preferences. For example, melancholic situations called for sad and moody music, while an arousing situation such as exercising would call for loud volume, a strong rhythm, and otherwise invigorating music.

Women are more likely than men to respond to music in a more emotional way. Furthermore, females prefer popular music and other 'softer' styles more than males. In a study of personality and gender in preference for exaggerated bass in music, researchers found that males demonstrated more of a preference for bass music than females. This preference for bass music is also correlated with antisocial and borderline personalities.

Age is a strong factor in determining music preference across the life span. Several studies indicate that preferences for music (and other commercial objects) apparently crystallize around the age of 16-24 years. In another study concerning how adolescent music preferences relate to personality, researchers found that adolescents who preferred heavy music demonstrated low self-esteem, higher levels of discomfort within the family, and tended to feel rejected by others. Adolescents who preferred light music were preoccupied with doing the proper thing, and had difficulty balancing independence with dependence. Adolescents who had eclectic music preferences had less difficulty negotiating adolescence, and were flexible using music according to mood and particular needs at the time.

The season of the year can also affect preferences. After reflecting upon fall or winter seasons, participants preferred reflective and complex music, whereas after reflecting upon summer or spring, participants preferred energetic and rhythmic music. However, "pop" music seems to have a universal appeal, despite the season.

Familiarity and complexity both have interesting effects on musical preferences. As seen in other types of artistic media, an inverted U relationship is apparent when relating subjective complexity to liking for music excerpts, such that intermediate levels of complexity are most popular. Furthermore, some researchers have argued that there is a clear positive monotonic relationship between familiarity and liking of music, whereas others claim that this relationship takes the form of an inverted-U.

Music preferences can also be influenced by how the individual wants to be perceived by others, especially in males. Music preferences could be used to make self-directed identity claims. Individuals might also select styles of music that reinforce their self-concept: for example, individuals with a conservative self-concept preferred conventional styles of music, while individuals with an athletic self-concept preferred vigorous music.

Active mood is another factor that affects music preference. Generally, whether people are in a good or bad mood when they hear music affects how they feel about the type of music and also their emotional response. Similarly, aggression has been shown to improve creativity and the emotional intensity perceived in music. People with aggressive disorders find music to be a powerful emotional outlet. Additionally, the value people put on music and frequency of listening affects their reactions to it.

Figure 5:
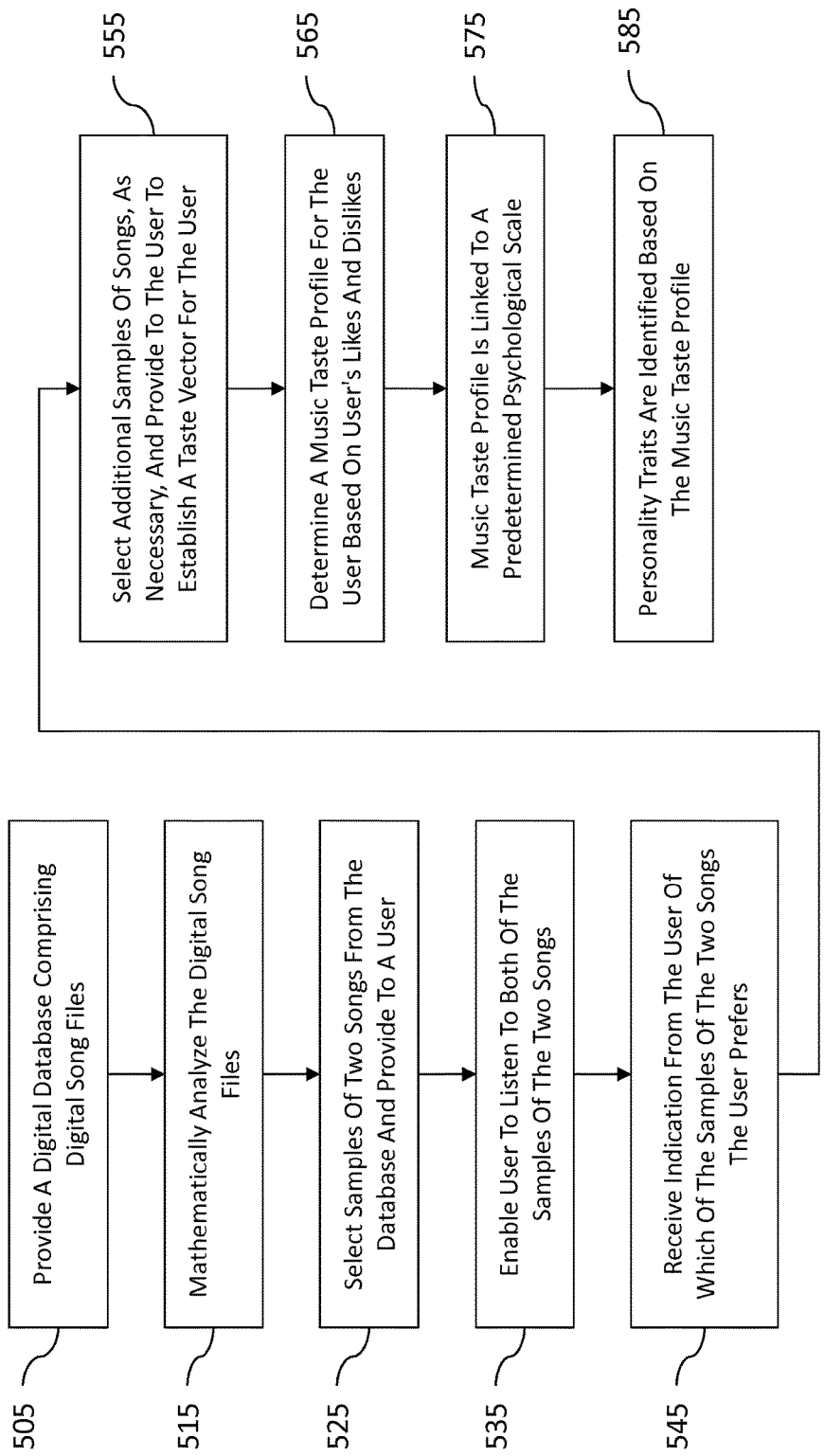
FIG. 5 is a flow chart according to systems and methods herein.

FIG. 5 is a flow diagram illustrating the processing flow of an exemplary method of determining psychological evaluation based on music preferences according to systems and methods herein. At 505, a digital database is provided. The digital database comprises digital song files. The digital song files are mathematically analyzed, at 515. The mathematical analysis determines a numerical value for each of a plurality of selected quantifiable characteristics of the songs. The quantifiable characteristics comprise physical parameters based on human perception. At 525, samples of two songs are selected from the database and provided to a user. The user is enabled to listen to both of the samples of the two songs, at 535. At 545, an indication is received from the user of which of the samples of the two songs the user prefers. Additional samples of songs are selected, as necessary, and provided to the user in order to establish a taste vector for the user, at 555. The taste vector comprises song characteristics that the user prefers. At 565, a music taste profile is determined for the user based on the user's likes and dislikes. At 575, the music taste profile is linked to a predetermined psychological scale. Personality traits are identified based on the music taste profile, at 585.

The systems and methods herein may be implemented with a smartphone app and/or web browser plug-in and web application. Users will use the application to listen to music either stored on the device or streamed and ultimately be presented with a description of their personality type.

Aspects of the present disclosure are described herein with reference to flowchart illustrations and/or block diagrams of methods, apparatus (systems), and computer program products according to various systems and methods. It will be understood that each block of the flowchart illustrations and/or two-dimensional block diagrams, and combinations of blocks in the flowchart illustrations and/or block diagrams, can be implemented by computer program instructions. The computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

According to a further systems and methods herein, an article of manufacture is provided that includes a tangible computer readable medium having computer readable instructions embodied therein for performing the steps of the computer implemented methods, including, but not limited to, the methods illustrated herein. Any combination of one or more computer readable non-transitory medium(s) may be utilized. The non-transitory computer storage medium stores instructions, and a processor executes the instructions to perform the methods described herein. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium include the following: an electrical connection having one or more wires, a portable computer diskette, a hard disk, a random access memory (RAM), a Read-Only Memory (ROM), an Erasable Programmable Read-Only Memory (EPROM or Flash memory), an optical fiber, a magnetic storage device, a portable compact disc Read-Only Memory (CD-ROM), an optical storage device, a "plug-and-play" memory device, like a USB flash drive, or any suitable combination of the foregoing. In the context of this document, a computer readable storage medium may be any tangible medium that can contain, or store a program for use by or in connection with an instruction execution system, apparatus, or device. Any of these devices may have computer readable instructions for carrying out the steps of the methods described above.

The computer program instructions may be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

Furthermore, the computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

In case of implementing the systems and methods herein by software and/or firmware, a program constituting the software may be installed into a computer with dedicated hardware, from a storage medium or a network, and the computer is capable of performing various functions if with various programs installed therein.

It is expected that any person skilled in the art can implement the disclosed procedure on a computer, and verify the emergent scoring curve for various realizations of the parameters in this example model. The generalization of the procedure to real-world scenarios with other definitions for the similarity measure should be evident to any person skilled in the art.

Figure 6:
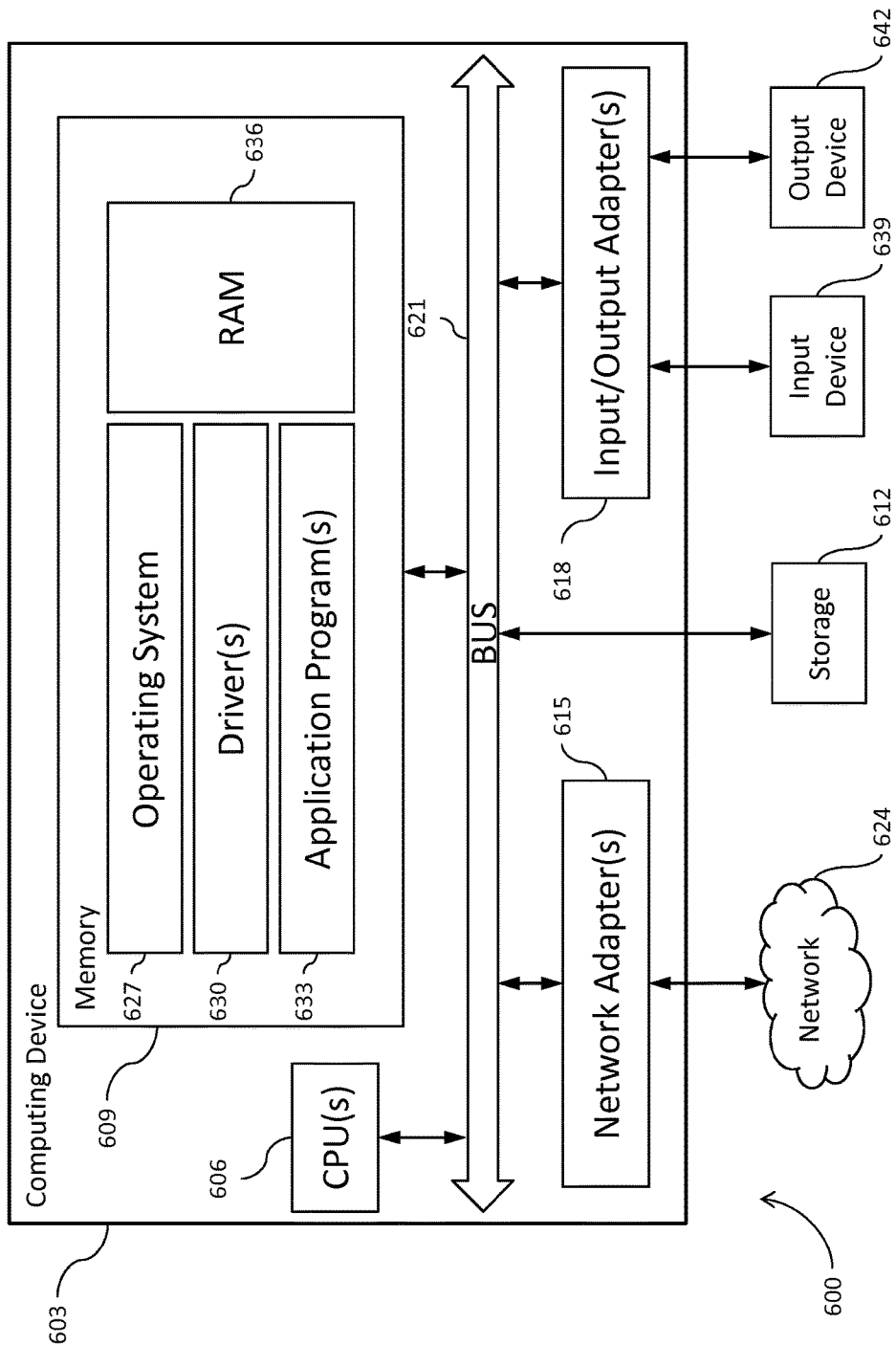
FIG. 6 is a schematic diagram of a hardware system according to systems and methods herein.

A representative hardware environment for practicing the systems and methods described herein is depicted in FIG. 6. This schematic drawing illustrates a hardware configuration of an information handling/computing system 600 in accordance with systems and methods herein. The computing system 600 comprises a computing device 603 having at least one processor or central processing unit (CPU) 606, internal memory 609, storage 612, one or more network adapters 615, and one or more Input/Output adapters 618. A system bus 621 connects the CPU 606 to various devices such as the internal memory 609, which may comprise Random Access Memory (RAM) and/or Read-Only Memory (ROM), the storage 612, which may comprise magnetic disk drives, optical disk drives, a tape drive, etc., the one or more network adapters 615, and the one or more Input/Output adapters 618. Various structures and/or buffers (not shown) may reside in the internal memory 609 or may be located in a storage unit separate from the internal memory 609.

The one or more network adapters 615 may include a network interface card such as a LAN card, a modem, or the like to connect the system bus 621 to a network 624, such as the Internet. The network 624 may comprise a data processing network. The one or more network adapters 615 perform communication processing via the network 624.

The internal memory 609 stores an appropriate Operating System 627, and may include one or more drivers 630 (e.g., storage drivers or network drivers). The internal memory 609 may also store one or more application programs 633 and include a section of Random Access Memory (RAM) 636. The Operating System 627 controls transmitting and retrieving packets from remote computing devices (e.g., host computers, database storage systems, etc.) over the network 624. The driver(s) 630 execute in the internal memory 609 and may include specific commands for the network adapter 615 to communicate over the network 624. Each network adapter 615 or driver 630 may implement logic to process packets, such as a transport protocol layer to process the content of messages included in the packets that are wrapped in a transport layer, such as Transmission Control Protocol (TCP) and/or Internet Protocol (IP).

The storage 612 may comprise an internal storage device or an attached or network accessible storage. Storage 612 may include disk units and tape drives, or other program storage devices that are readable by the system. A removable medium, such as a magnetic disk, an optical disk, a magneto-optical disk, a semiconductor memory, or the like, may be installed on the storage 612, as necessary, so that a computer program read therefrom may be installed into the internal memory 609, as necessary. Programs in the storage 612 may be loaded into the internal memory 609 and executed by the CPU 606. The Operating System 627 can read the instructions on the program storage devices and follow these instructions to execute the methodology herein.

The Input/Output adapter 618 can connect to peripheral devices, such as input device 639 to provide user input to the CPU 606. The input device 639 may include a keyboard, mouse, pen-stylus, microphone, touch sensitive display screen, or any other suitable user interface mechanism to gather user input. An output device 642 can also be connected to the Input/Output adapter 618, and is capable of rendering information transferred from the CPU 606, or other component. The output device 642 may include a display monitor (such as a Cathode Ray Tube (CRT), a Liquid Crystal Display (LCD), or the like), printer, speaker, etc.

The computing system 600 may comprise any suitable computing device 603, such as a mainframe, server, personal computer, workstation, laptop, handheld computer, telephony device, network appliance, virtualization device, storage controller, etc. Any suitable CPU 606 and Operating System 627 may be used. Application Programs 633 and data in the internal memory 609 may be swapped into storage 612 as part of memory management operations.

The hardware described herein plays a significant part in permitting the foregoing methods to be performed, rather than function solely as a mechanism for permitting a solution to be achieved more quickly, (i.e., through the utilization of a computer for performing calculations). As would be understood by one ordinarily skilled in the art, the processes described herein cannot be performed by human alone (or one operating with a pen and a pad of paper) and instead such processes can only be performed by a machine. Specifically, processes such as automatically analyzing input music tracks, automatically associating input tracks according to psychometric analysis, and automatically creating highly personalized, relevant recommendation for the user use different specialized machines and cannot be performed by humans alone.

Additionally, the methods herein solve many highly complex technological problems. For example, as mentioned above, the system produces a profile based on the determined personality type. That is, the systems and methods herein provide the ability to identify the listener's musical preferences and link this to a predetermined profile.

As will be appreciated by one skilled in the art, aspects of the systems and methods herein may be embodied as a system, method, or computer program product. Accordingly, aspects of the present disclosure may take the form of an entirely hardware system, an entirely software system (including firmware, resident software, micro-code, etc.) or an system combining software and hardware aspects that may all generally be referred to herein as a "circuit," "module," or "system." Furthermore, aspects of the present disclosure may take the form of a computer program product embodied in one or more computer readable medium(s) having computer readable program code embodied thereon.

Computer program code for carrying out operations for aspects of the present disclosure may be written in any combination of one or more programming languages, including an object oriented programming language such as Java, Smalltalk, C++, or the like and conventional procedural programming languages, such as the "C" programming language or similar programming languages. The program code may execute entirely on the user's computer, partly on the user's computer, as a stand-alone software package, partly on the user's computer and partly on a remote computer, or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Program code embodied on a computer readable medium may be transmitted using any appropriate medium, including, but not limited to, wireless, wireline, optical fiber cable, RF, etc., or any suitable combination of the foregoing.

The flowchart and block diagrams in the figures illustrate the architecture, functionality, and operation of possible implementations of systems, methods, and computer program products according to various systems and methods herein. In this regard, each block in the flowchart or block diagrams may represent a module, segment, or portion of code, which comprises one or more executable instructions for implementing the specified logical function(s). It should also be noted that, in some alternative implementations, the functions noted in the block might occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular systems and methods only and is not intended to be limiting of this disclosure. As used herein, the singular forms "a", "an", and "the" are intended to include the plural forms as well, unless the context clearly indicates otherwise. It will be further understood that the terms "comprises," "comprising," and/or "including," when used in this specification, specify the presence of stated features, integers, steps, operations, elements, and/or components, but do not preclude the presence or addition of one or more other features, integers, steps, operations, elements, components, and/or groups thereof. Further, the terms "automated" or "automatically" mean that once a process is started (by a machine or a user), one or more machines perform the process without further input from any user.

In addition, terms such as "right", "left", "vertical", "horizontal", "top", "bottom", "upper", "lower", "under", "below", "underlying", "over", "overlying", "parallel", "perpendicular", etc., used herein are understood to be relative locations as they are oriented and illustrated in the drawings (unless otherwise indicated). Terms such as "touching", "on", "in direct contact", "abutting", "directly adjacent to", etc., mean that at least one element physically contacts another element (without other elements separating the described elements).

While particular values, relationships, materials, and steps have been set forth for purposes of describing concepts of the systems and methods herein, it will be appreciated by persons skilled in the art that numerous variations and/or modifications may be made to the systems and methods as shown in the disclosure without departing from the spirit or scope of the basic concepts and operating principles of the concepts as broadly described. It should be recognized that, in the light of the above teachings, those skilled in the art could modify those specifics without departing from the concepts taught herein. Having now fully set forth certain systems and methods, and modifications of the concepts underlying them, various other systems and methods, as well as potential variations and modifications of the systems and methods shown and described herein will obviously occur to those skilled in the art upon becoming familiar with such underlying concept. It is intended to include all such modifications and alternatives insofar as they come within the scope of the appended claims or equivalents thereof. It should be understood, therefore, that the concepts disclosed might be practiced otherwise than as specifically set forth herein. Consequently, the present systems and methods are to be considered in all respects as illustrative and not restrictive.

The corresponding structures, materials, acts, and equivalents of all means or step plus function elements in the claims below are intended to include any structure, material, or act for performing the function in combination with other claimed elements as specifically claimed. The descriptions of the various systems and methods herein have been presented for purposes of illustration, but are not intended to be exhaustive or limited to the systems and methods disclosed. Many modifications and variations will be apparent to those of ordinary skill in the art without departing from the scope and spirit of the described systems and methods. The terminology used herein was chosen to best explain the principles of the systems and methods, the practical application or technical improvement over technologies found in the marketplace, or to enable others of ordinary skill in the art to understand the systems and methods disclosed herein.

What is claimed is:

1. A method comprising:
   providing a database comprising digital song files;
   mathematically analyzing said digital song files, using a computerized device, said mathematically analyzing determining a numerical value for each of a plurality of selected quantifiable characteristics, each of said quantifiable characteristics comprising a physical parameter based on human perception;
   creating a descriptive profile for the quantifiable characteristics of each song in the database of digital song files, using said computerized device;
   linking each song in the database to a predetermined psychological scale based on said descriptive profile for the quantifiable characteristics, using said computerized device;
   providing pairs of audible samples of songs to a user, using said computerized device, each sample of said pairs audible samples being selected from said database of digital song files;
   permitting said user to listen to each sample of said pair of audible samples of songs and subjectively indicate, using said computerized device, likes and dislikes for each song of said samples of songs;
   said computerized device determining a music taste profile for said user based on said likes and dislikes indicated by said user, wherein said music taste profile identifies relative preferences for genre, theme, and style of music for said user;
   correlating said relative preferences to known dimensions of said predetermined psychological scale for said user by associating said relative preferences with a plurality of lifestyle factors for said user, using said computerized device; and
   identifying distinct human psychological traits, based on said music taste profile to classify said user into a known personality type.

2. The method according to claim 1, said mathematically analyzing said digital song files further comprising:
   compiling a song vector comprising a list of numerical values for each of said plurality of selected quantifiable characteristics for each said digital song file; and
   extracting a plurality of music descriptors for each song vector.

3. The method according to claim 2, said mathematically analyzing said digital song files further comprising:
   using fast Fourier Transform techniques to establish a plurality of sonic coefficients, said sonic coefficients being representative of said characteristics of said song.

4. The method according to claim 1, further comprising:
   choosing two dissimilar samples of songs from said database;
   enabling said user to listen to both of said two dissimilar samples of songs;
   receiving an indication of which of said two dissimilar samples of songs said user prefers; and
   choosing additional dissimilar samples of songs, as necessary, to establish a taste vector for said user comprising song characteristics that said user prefers.

5. The method according to claim 1, said predetermined psychological scale comprising:
   openness;
   conscientiousness;
   extraversion;
   agreeableness; and
   neuroticism.

6. The method according to claim 1, said identifying human psychological traits further comprising:
   identifying personality triggers from said music taste profile;
   linking said personality triggers to a dictionary of descriptors defining a personality type according to musical tastes; and
   producing a personal profile based on a determined personality type.

7. The method according to claim 1, further comprising:
   providing recommendations based on said music taste profile and said personality type, said recommendations being related to one of music, films, television, and books.

8. The method according to claim 1, said method being performed using a real-time process based on dynamic interaction with said user.

9. A computer implemented method of determining psychological evaluation based on music preferences, said method comprising:
   providing a database comprising digital song files;
   mathematically analyzing said digital song files, using a computerized device, said mathematically analyzing determining a numerical value for each of a plurality of selected quantifiable characteristics, said quantifiable characteristics comprising physical parameters based on human perception;
   creating a descriptive profile for the quantifiable characteristics of each song in the database of digital song files, using said computerized device;
   linking each song in the database to a predetermined psychological scale based on said descriptive profile for the quantifiable characteristics, using said computerized device;
   choosing samples of two songs from said database, using said computerized device;
   enabling a user to listen to both of said samples of two songs, using said computerized device;
   receiving an indication of which of said samples of two songs said user prefers, using said computerized device;
   choosing additional samples of songs, as necessary, to establish a taste vector for said user comprising song characteristics that said user prefers, using said computerized device;

determining a music taste profile for said user based on likes and dislikes indicated by said user, wherein said music taste profile identifies relative preferences for genre, theme, and style of music for said user, using said computerized device;

correlating said relative preferences to known dimensions of said predetermined psychological scale for said user by associating said relative preferences with a plurality of lifestyle factors for said user, using said computerized device;

identifying distinct human psychological traits, based on said music taste profile, using said computerized device; and classifying said user into a known personality type, using said computerized device.

10. The computer implemented method according to claim 9, further comprising:

providing recommendations to said user based on said music taste profile and said personality type, using said computerized device, said recommendations being related to one of music, films, television, and books.

11. The computer implemented method according to claim 9, said mathematically analyzing said digital song files further comprising:

compiling a song vector comprising a list of numerical values for each of said plurality of selected quantifiable characteristics for each said digital song file; and extracting a plurality of music descriptors for each song vector.

12. The computer implemented method according to claim 11, said mathematically analyzing said digital song files further comprising:

using fast Fourier Transform techniques to establish a plurality of sonic coefficients, said sonic coefficients being representative of said characteristics of said song.

13. The computer implemented method according to claim 9, said identifying human psychological traits further comprising:

identifying personality triggers from said music taste profile;

linking said personality triggers to a dictionary of descriptors defining a personality type according to musical tastes; and producing a personal profile based on a determined personality type, said human psychological traits being based on said music taste profile.

14. The computer implemented method according to claim 9, said method being performed using a real-time process based on dynamic interaction with said user.

15. A system comprising:

a digital database comprising digital song files;

a processor operatively connected to said digital database; and a user interface operatively connected to said processor;

said processor mathematically analyzing said digital song files and determining characteristic vectors for songs in said digital song files, said characteristic vectors comprising a numerical value for each of a plurality of selected quantifiable characteristics, each of said quantifiable characteristics comprising a physical parameter based on human perception, said processor creating a descriptive profile for the quantifiable characteristics of each song in the digital database of digital song files, said processor linking each song in the digital database to a predetermined psychological scale based on said descriptive profile for the quantifiable characteristics, said processor selecting samples of two songs from said database and enabling a user to listen to both of said samples of two songs using said user interface, said processor receiving an indication of which of said samples of two songs said user prefers, using said user interface, said processor selecting additional samples of songs, as necessary, to establish a taste vector for said user comprising song characteristics that said user prefers, said processor determining a music taste profile for said user based on likes and dislikes for said samples of songs, and said user's age, sex, and location, wherein said music taste profile identifies relative preferences for genre, theme, and style of music for said user, said processor correlating said relative preferences to known dimensions of said predetermined psychological scale for said user by associating said relative preferences with a plurality of lifestyle factors for said user, and said processor identifying distinct human psychological traits, based on said music taste profile to classify said user into a known personality type.

16. The system according to claim 15, further comprising:

said processor providing recommendations to said user on said user interface, said recommendations being based on said music taste profile and said personality type.

17. The system according to claim 16, said recommendations being related to one of music, films, television, books, leisure time interests, means of advertising, and otherwise communicating with consumers.

18. The system according to claim 15, said processor mathematically analyzing said digital song files further comprising:

said processor compiling a song vector comprising a list of numerical values for each of said plurality of selected quantifiable characteristics for each said digital song file; and said processor extracting a plurality of music descriptors for each song vector.

19. The system according to claim 18, said processor mathematically analyzing said digital song files further comprising:

said processor using fast Fourier Transform techniques to establish a plurality of sonic coefficients, said sonic coefficients being representative of said characteristics of said song.

20. The system according to claim 15, said processor identifying human psychological traits further comprising:

said processor identifying personality triggers from said music taste profile;

said processor linking said personality triggers to a dictionary of descriptors defining a personality type according to musical tastes; and said processor producing a personal profile based on a determined personality type, said human psychological traits being based on said music taste profile.

* * * * *